United States Patent
Proksa et al.

(10) Patent No.: US 7,826,585 B2
(45) Date of Patent: Nov. 2, 2010

(54) STEREO TUBE COMPUTED TOMOGRAPHY

(75) Inventors: Roland Proksa, Hamburg (DE); Andy Ziegler, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 53 days.

(21) Appl. No.: 12/375,427

(22) PCT Filed: Jul. 23, 2007

(86) PCT No.: PCT/US2007/074091
§ 371 (c)(1),
(2), (4) Date: Jan. 28, 2009

(87) PCT Pub. No.: WO2008/021661
PCT Pub. Date: Feb. 21, 2008

(65) Prior Publication Data
US 2010/0002830 A1    Jan. 7, 2010

Related U.S. Application Data

(60) Provisional application No. 60/820,963, filed on Aug. 1, 2006.

(51) Int. Cl.
G01N 23/083    (2006.01)
G01N 23/087    (2006.01)

(52) U.S. Cl. .............................. 378/9; 378/5

(58) Field of Classification Search ............ 378/5, 378/9
See application file for complete search history.

(56) References Cited

U.S. PATENT DOCUMENTS

| | | | | |
|---|---|---|---|---|
| 4,592,079 A | * | 5/1986 | Sohval et al. ............ | 378/9 |
| 5,625,661 A | * | 4/1997 | Oikawa ................... | 378/15 |
| 5,966,422 A | | 10/1999 | Dafni et al. | |
| 6,118,839 A | | 9/2000 | Darni et al. | |
| 6,256,369 B1 | * | 7/2001 | Lai ........................ | 378/14 |
| 6,421,412 B1 | * | 7/2002 | Hsieh et al. ............. | 378/9 |
| 6,804,325 B1 | * | 10/2004 | Smith ..................... | 378/37 |
| 7,103,138 B2 | * | 9/2006 | Pelc et al. ............... | 378/9 |
| 7,308,072 B2 | * | 12/2007 | Ruhrnschopf ........... | 378/7 |
| 7,639,774 B2 | * | 12/2009 | De Man et al. ......... | 378/9 |

(Continued)

FOREIGN PATENT DOCUMENTS

WO    0206134 A    4/2002

(Continued)

OTHER PUBLICATIONS

Yu, Daniel F., Fessler, Jeffrey A.; Maximum-Likelihood Transmission Image Reconstruction for Overlapping Transmission Beams; 2000; IEEE Trans. on Medical Imaging; 19(11)1094-1105.

*Primary Examiner*—Edward J Glick
*Assistant Examiner*—Thomas R Artman

(57) ABSTRACT

A computed tomography system includes at least two x-ray sources (108), a at least one common detector (124), and a reconstruction system (136). The at least two x-ray sources (108) are aligned at different z-axis locations at about a same angular position and concurrently emit radiation that traverses an imaging region (116). The at least one detector (124) detects radiation emitted by the at least two x-ray source (108) and generates composite data indicative of the detected radiation. The reconstruction system (136) reconstructs the composite data to generate one or more images.

20 Claims, 3 Drawing Sheets

U.S. PATENT DOCUMENTS

2003/0053597 A1  3/2003  Flohr et al.
2003/0108146 A1  6/2003  Malamud
2005/0058242 A1* 3/2005  Peschmann .................. 378/57
2006/0285633 A1* 12/2006 Sukovic et al. ................. 378/9

FOREIGN PATENT DOCUMENTS

WO    0226134 A1    4/2002

* cited by examiner

STEREO TUBE COMPUTED TOMOGRAPHY

CROSS REFERENCE TO RELATED APPLICATIONS

This application claims the benefit of U.S. provisional application Ser. No. 60/820,963 filed Aug. 1, 2006, which is incorporated herein by reference.

The present application relates to medical imaging systems. It finds particular application to computed tomography (CT) and, more particularly to stereo tube CT imaging techniques.

An exemplary CT system may include an x-ray tube mounted on a gantry opposite one or more detectors. During scanning, the x-ray tube emits radiation that traverses an imaging region and strikes the one or more detectors, which generate signals indicative of the detected radiation. The resulting signals are reconstructed to generate volumetric data, which is used to produce one or more images of a scanned region of a subject residing within the imaging region.

Axial scan protocols can be used with such systems to serially capture finite regions or slices of the subject. However, the width of the detector limits the width of the region of the subject that can be imaged during each scan. This may be coverage prohibitive, for example, when desiring to capture a part of a structure or a whole structure that is larger than the detector width. In order to capture data representative of a relatively larger region of the subject, a helical (or spiral) scan can be performed. With helical scans, the subject may be continuously moved through the imaging region via a mobile support or couch while the x-ray tube rotates around the imaging region and data is collected. The resulting data may be representative of structure with a size that exceeds the width of the detector(s). However, helical data acquisitions may take more time than axial data acquisitions due to couch ramp up delays, multiple x-ray source revolutions, etc.

With some CT applications, it is often desirable to capture a relatively large region of anatomy (e.g., a whole organ) in a relatively short period of time in order to reconstruct such anatomy at a higher temporal resolution. With the system described above, an axial scan protocol may not provide the coverage to acquire the desired volume of interest in a single axial scan. A helical scan protocol may provide the desired coverage, however, at the cost of time. As a consequence, temporal resolution may decrease and motion artifact may increase relative to an axial scan.

Cone beam CT systems using one or more large area detectors allow scanning of relatively larger volumes of anatomy (e.g., whole organs) with axial scan protocols. However, the data acquisition is limited in that conventional axial cone beam CT scanning techniques fail to provide complete sampling. As a result, the images generated from such data may include inherent artifacts such as streaking. The deficiency in data can be theoretically or mathematically determined and mitigated by using two x-ray sources in a stereo tube configuration and combining the detected data.

In a stereo tube configuration, at least two x-ray sources are positioned at the same angular position along different z-axis locations and share a common detector(s) for data acquisition. Since the detector(s) is shared, the x-ray sources have been sequentially (alternately) switched "on" and "off" such that radiation from only one of the x-ray sources illuminates the shared detector(s) at any given time. With a stereo tube system, both of the x-ray sources move out of the image plane during some portion of the axial scan. However, by suitably combing the detected data a data set with enough data for reconstruction with a traditional cone beam CT reconstruction algorithm can be generated. This data set can be reconstructed and used for generating one or more images.

However, operating the x-ray sources in such a sequential manner has various drawbacks. For example, a grid switch, a gate, a shutter or the like is used to quickly and accurately switch the tubes "on" and "off." Such devices, together with their requisite control systems, can add cost and complexity to the system. In addition, since each x-ray source is only active for about half of the time, the average photon flux generated by each x-ray source may only be about half of the maximal photon flux relative to a continuously "on" x-ray source. As a consequence, the power may have to be increased (e.g., doubled) to achieve a photon flux and signal-to-noise ratio (SNR) similar to that of a system with a continuously "on" x-ray source, and this may not be feasible since conventional x-ray sources generally are power limited. Furthermore, x-ray sources driven in a sequential mode typically cannot be switched completely "off" such that no radiation is emitted. As a consequence, residual photon flux from the "off" x-ray source may contaminate the signal of the "on" x-ray source. Moreover, afterglow of the detector(s) may have a relatively greater effect since temporal cross-talk of the different x-ray sources can be relatively stronger.

Aspects of the present application address the above-referenced problems and others.

According to one aspect, a computed tomography system includes at least two x-ray sources, at least one common detector, and a reconstruction system. The at least two x-ray sources are aligned at different z-axis locations at about a same angular position and concurrently emit radiation that traverses an imaging region. The at least one common detector detects radiation emitted by the at least two x-ray source and generates composite data indicative of the detected radiation. The reconstruction system reconstructs the composite data to generate one or more images.

According to another aspect, a computed tomography method is illustrated. The computed tomography method includes concurrently emitting radiation by at least two x-ray sources positioned at different z-axis locations at about a same angular position around an imaging region that traverses the imaging region, detecting the radiation from the at least two x-ray sources with at least one common detector, generating composite data indicative of the detected radiation, and reconstructing the composite data to form an image.

According to another aspect, a computed tomography imaging system includes a means for concurrently emitting radiation by at least two x-ray sources aligned in a stereo tube configuration, a means for concurrently detecting the radiation from the at least two x-ray sources, a means for generating a signal indicative the detected radiation from the at least two x-ray sources, and a means for reconstructing the signal having contributions from both of the least two x-ray sources to generate an image.

The invention may take form in various components and arrangements of components, and in various steps and arrangements of steps. The drawings are only for purposes of illustrating the preferred embodiments and are not to be construed as limiting the invention.

Figure 1:
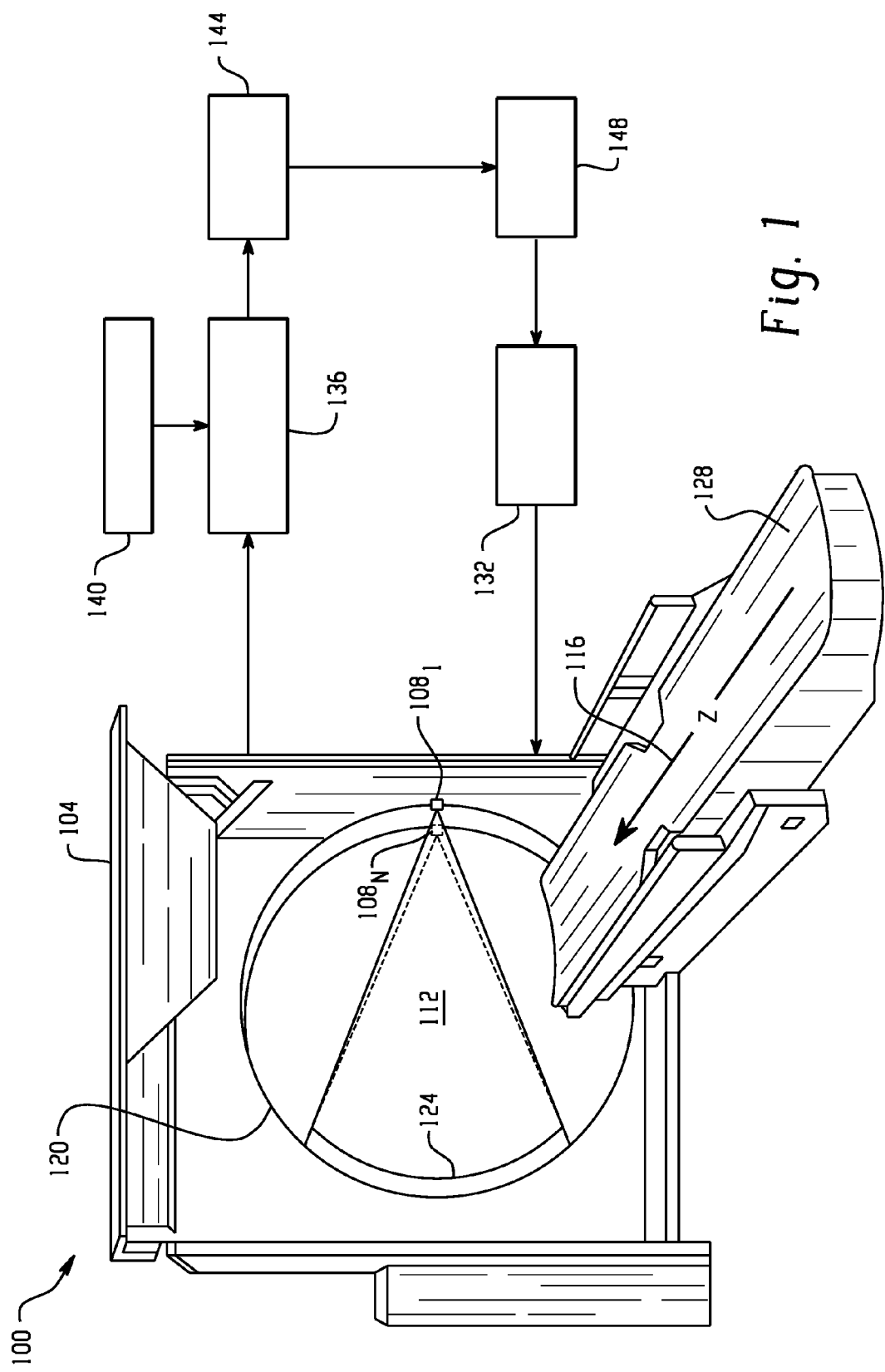
FIG. 1 illustrates a multi-source medical imaging system that employs concurrently emitting x-rays sources arranged in a stereo tube configuration.

With reference to FIG. 1, a medical imaging system 100 includes a scanner 104 having N x-ray sources $108_1$, $108_N$ (collectively referred to herein as x-ray sources 108), wherein N is an integer greater than one. The x-ray sources 108 can be used to generate a cone beam, a fan beam, or other beam geometries. In addition, each of the x-ray sources 108 can produce and emit radiation having a similar or different spectral distribution, intensity, and/or other characteristics.

As depicted, the x-ray sources 108 reside at about a same angular position about an imaging region 112 and are offset along a z-axis 116. It is to be appreciated that in another embodiment the at least two of the x-ray sources 108 can be positioned at different angular positions and offset along the z-axis 116. In yet another embodiment, the at least two of the x-ray sources 112 can be positioned at different angular positions and at about the same location on the z-axis 116.

In one instance, the x-ray sources 108 are disposed about a rotating gantry 120. In such instance, rotating the gantry 120 about the imaging region 112 rotates the x-ray sources 108 about the imaging region 112. It is to be appreciated that such x-ray sources 108 may originate within separate x-ray tubes that are physically attached to the gantry 120. Such x-ray tubes can be positioned as described above, for example, such that the x-ray sources 108 are at about the same angular position and offset along the z-axis 116. Conventional beam controlling electronics can be used to accurately control the x-ray sources 108 to compensate for any differences in relative physical position with respect to the angular positioning of the x-ray tubes.

In another implementation, the x-ray sources 108 can originate from different foci within the same tube. Likewise, this tube can be physically attached to the gantry 120 and the radiation emitted from each of the foci can be controlled accordingly by electronics to accurately position the x-ray sources 108. In another instance, the system 112 may have a combination of tubes in which one or more have a single one of the x-ray sources 108 and one or more have multiple ones of the x-ray sources 108. In another instance, the x-ray sources 108 are generated by a device(s) separate from the gantry 120. For instance, the x-ray sources 108 can be produced from an electron beam generator or gun that controls the position of an e-beam through electronic deflection or the like.

The scanner 104 further includes one or more detectors 124 ("detectors 124"), wherein each of the detectors 124 have at least one detector element. It is to be appreciated that each of the detectors 124 may be different or similar in dimension, energy resolution, shape, etc. In one instance, at least one of the detectors 124 is a large area detector. As such, the detectors 124 may include two-dimensional detectors with two or more detector elements. Using such detectors 124 enables larger volumes, widths, regions of interest or the like within a subject to be scanned using axial scan protocols relative to one-dimensional detectors.

Such scanning capabilities can be leveraged to quickly acquire data representative of larger areas or whole organs in a single axial scan. This facilitates acquiring relatively high temporal resolution data with relatively broad coverage, if desired. In addition, such scanning can be used in connection with functional imaging such as perfusion imaging in which a contrast(s) or other agent(s) quickly moves through tissue of interest, metabolic imaging, and the like.

Each of the detectors 124 may be based on different or similar detector technologies. Examples of suitable technologies include, but are not limited to, indirect conversion technology (e.g., incorporating a gadolinium oxysulphide (GOS) scintillator), direct conversion technology (e.g., incorporating crystalline cadmium zinc telluride (CZT)) material), or other technologies.

As depicted, the detectors 124 subtend an angular arc opposite the x-ray sources 108, and the imaging region 112 is defined therebetween. In one instance, each of the detectors 124 rotates along with the x-ray sources 108, for example, as with a third generation CT system. In another instance, the detectors 124 reside at a static angular location about a stationary gantry. In such instance, the detectors 124 detected radiation at any moment in time are determined by the angular position of the x-ray sources 108, for example, as with a fourth generation CT system.

The detectors 124 detect radiation emitted by the x-ray sources 108. Anti-scatter grids or the like can be used to reduce the detection of scatter radiation.

A support 128 supports a subject, such as a human, within the imaging region 112. The support 128 may be movable in order to guide the subject to a suitable location within the imaging region 112 before, during and/or after performing a helical, axial, and/or other scan, for example, by moving the support 128 along the z-axis 116 and/or one or more other axes.

A control component 132 controls each of the x-ray sources 108. Such control includes, but is not limited to, activating the x-ray sources 108 to emit radiation during scanning and deactivating the x-ray sources 108 to terminate such emission. In one instance, the control component 132 controls the x-ray sources 108 such that at least two of the x-ray sources 108 concurrently emit radiation during data acquisition. During data acquisition, the concurrently emitting x-ray sources 108 typically are driven with about the same power, for example, each can be driven with the same power used in systems with a single continuously emitting x-ray source.

Since each of the x-ray sources 108 is continuously driven to emit radiation, the peak power of the photon flux and the signal-to-noise ratio (SNR) for each of the x-ray sources 108 is as if it were the only x-ray source emitting radiation. With conventional approaches, the x-ray sources typically are alternately activated, which can result in a reduction of photon flux and increased noise at the same power level. In addition, grid switches, gates, shutters, and the like are not needed to switch the x-ray sources 108 "on" and "off" during data acquisition when it is not necessary to switch the x-ray sources 108. However, such components can be implemented when needed or desired. Moreover, temporal resolution can be increased relative alternately operating the sources since more data is obtained in about the same amount of time.

When multiple x-ray sources 108 are concurrently emitting radiation, however, the radiation beams overlap and each of the detectors 124 concurrently detects radiation emitted by more than one of the x-ray sources 108. Since the x-ray sources 108 are located at different locations along the z-axis 116, the radiation emitted thereby travels through different paths through the imaging region 116 and represents different information.

Figure 3:
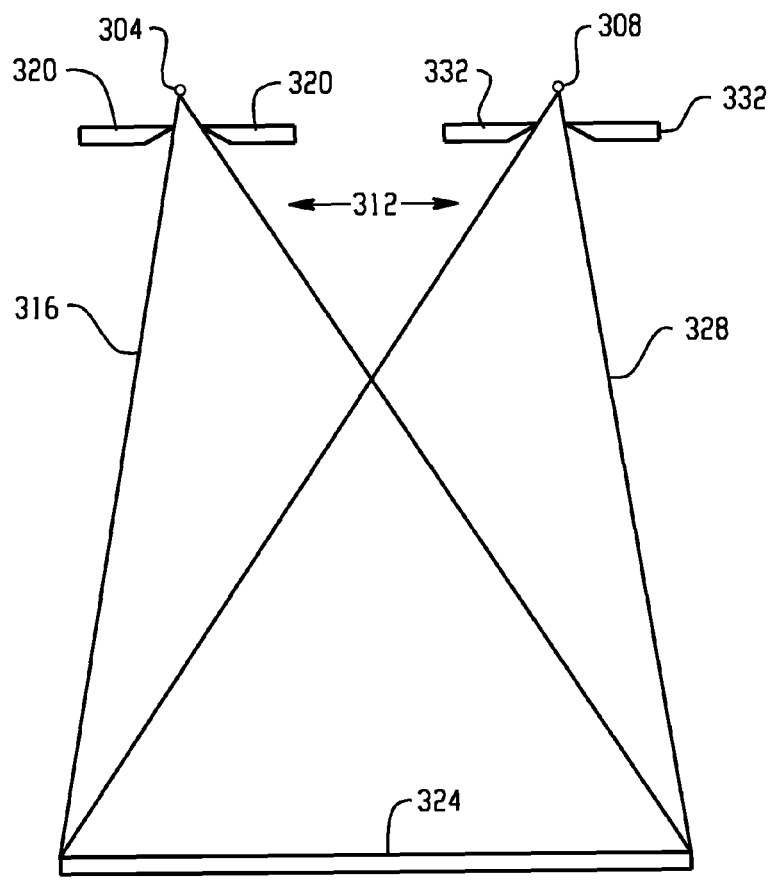
FIG. 3 illustrates two x-ray sources in a stereo tube configuration emitting beams that overlap and strike a common detector.

The above is illustrated in FIG. 3, wherein x-ray sources 304 and 308 are positioned at different positions along a z-axis 312. A beam 316 emitted by the x-ray source 304 is collimated by collimators 320 and illuminates a portion of a common detector 324. Concurrently, a beam 328 emitted by the x-ray source 308 is collimated by collimators 332 and illuminates a portion of the common detector 324. As depicted, the beams 304 and 308 overlap on the common detector 324.

Returning to FIG. 1, if needed, the dynamic range of the detectors 124 can be suitably configured by conventional techniques based on the number of x-ray sources 108 concurrently emitting radiation since each x-ray source 108 contributes to the x-ray intensity seen by the detectors 124.

Upon detecting radiation from the x-ray sources 108, each of the detectors 124 generates a signal indicative of the detected radiation. Since radiation from multiple x-ray sources 108 is concurrently detected, the generated signals have contributions or components corresponding to each of the emitting x-ray sources 108.

Such signals are provided to a reconstruction system 136 for reconstruction of volumetric data indicative of the object. As described in greater detail below, the reconstruction system 136 has a multi-source reconstructor 140 that takes into account that each signal from the signal corresponding to the overlapping position of the detectors 124 is a composite signal with contributions from each of the N x-ray sources 108. It is to be appreciated that the reconstructor 140 can be hardware or software. In one instance, the reconstructor 140 includes a computer processor that executes computer readable instructions stored on computer readable medium.

An image processor 144 processes the reconstructed data to generate one or more images. The generated images can be displayed, filmed, archived, forwarded to a treating clinician (e.g., emailed, etc.), fused with images from other imaging modalities, further processed (e.g., via measurement and/or visualization utilities and/or a dedicated visualization system), stored, etc.

A computing system (or console) 148 facilitates operator interaction with and/or control of the scanner 104. Software applications executed by the computing system 148 allow the operator to configure and/or control operation of the scanner 104. For instance, the operator can interact with the computing system 148 to select scan protocols, initiate, pause and terminate scanning, view images, manipulating volumetric image data, measure various characteristics of the data (e.g., CT number, noise, etc.), etc. The computing system 148 also communicates various information to the control component 132.

Figure 4:
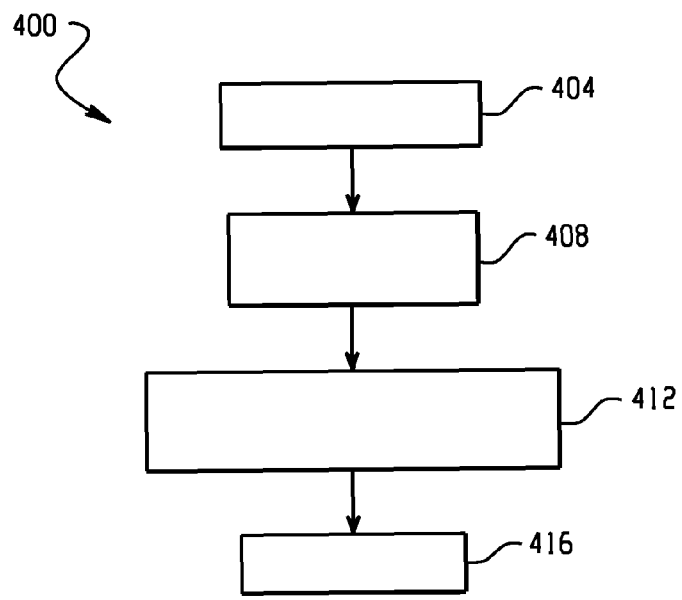
FIG. 4 illustrates an exemplary iterative reconstruction technique.

FIG. 4 illustrates an exemplary reconstruction approach 400 employed by the reconstructor 140. The system 100 can be modeled as a function of the N x-ray sources 108. In one instance, this is achieved by solving for the unknown attenuation coefficients in the attenuation map. For example, the unknown attenuation coefficients can be described and solved for in terms of line integrals or otherwise. The resulting function is a summation over the N x-ray sources 108 and accounts for arbitrary overlap of the x-ray beams on each of the detectors 124. This model can be used in connection with the following iterative reconstruction approach.

At 404, an initial image estimate for a stereo tube CT system simultaneously emitting radiation is generated. At 408, the image estimate is forward projected to generate projection data. At 412, the forward projection data is compared with an objective function. In one instance, the objective function is a log-likelihood of the above system model, which considers signals corresponding to multiple beam overlap. At 416, this comparison is used to adjust the image estimate. Various known techniques can be used to maximize the function to increase the likelihood with each iteration. For instance, an expectation-maximization approach can be used to monotonically increase the likelihood. Other suitable techniques include, but are not limited to, coordinated ascent, ordered subset, and paraboloidal approaches.

By way of example, in one non-limiting implementation a maximum likelihood function is used to sequentially update voxels during each iteration based on the N x-ray source contributions. With this example, the multi-source reconstructor 140 forward projects data for each of the N x-ray sources 108 each iteration. The forward projected data is adjusted and allocated to each of the N x-ray sources 108. This can be achieved through computing a difference between an aggregate of the forward projected data and the measured data and scaling the forward projected data based on this difference. The data is then backprojected for each source as a weighted function of the x-ray source contribution to the aggregate contribution. This accounts for the N x-ray sources 108. Each iteration is completed upon sequentially updating the voxels, and with each iteration, the allocation of the data updates and converges.

This process of forward projecting the estimated image, comparing the forward projected data to the objection function, and updating the estimated image continues until a desired level of agreement with the forward projected data is reached.

An example of such technique used in connection with a single photon emission tomography (SPECT) system is discussed in "Maximum Likelihood Transmission Image Reconstruction for Overlapping Transmission Beams," Fessler et al., IEEE Transaction on Medical Imaging, Vol. 19, No. 11, November 2000.

Figure 2:
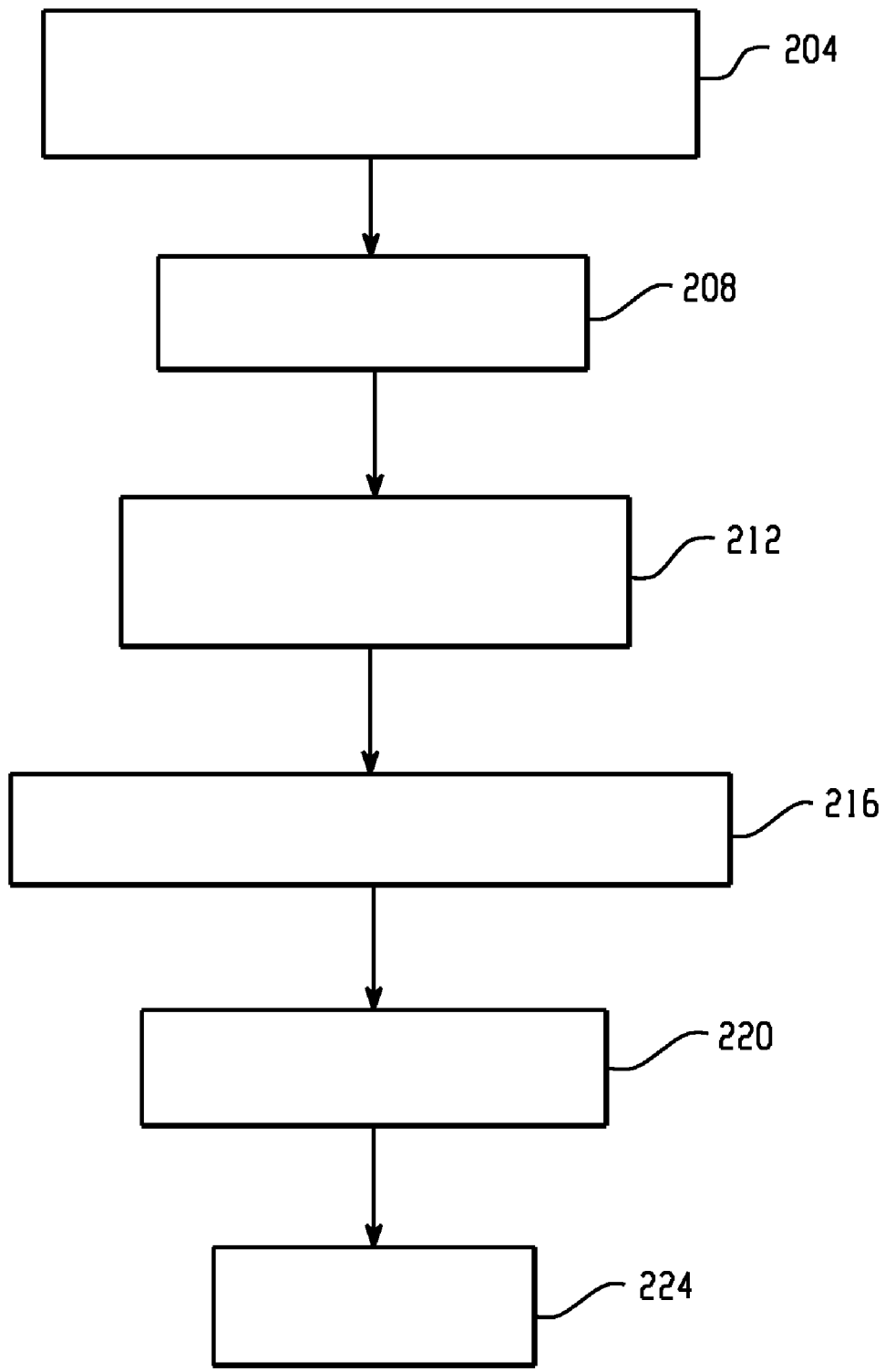
FIG. 2 illustrates an exemplary method for imaging with a multi-source medical imaging system that employs concurrently emitting x-rays sources arranged in a stereo tube configuration.

FIG. 2 illustrates a non-limiting method 200 for concurrently using at least two x-ray sources 108 in a stereo tube configuration to image a subject. Similar to the system 100, the x-ray sources 108 can be paired with the detectors 124 in a third, fourth, or other generation systems. With a stereo tube configuration, the x-ray sources 108 can be positioned such that they are at about a same angular position about the imaging region 112 and offset along the z-axis 116. However, other configurations as described above are also contemplated herein. In addition, the x-ray sources 108 may be attached to and rotate with the rotating gantry 120.

At reference numeral 204, at least two x-ray sources 108 concurrently generate and emit radiation through the imaging region 112. Such radiation can be cone beam, fan beam, or beams with other geometries. In addition, each of the x-ray sources 108 can emit radiation of similar or different spectral distribution, intensity, and/or other characteristics. At 208, the radiation from each of the x-ray sources 108 traverses the imaging region 112. Since the x-ray sources 108 reside at different z-axis locations, the radiation emitted by each of the x-ray sources 108 traverses a different path through the imaging region 116.

Upon traversing the imaging region 112, at 212 the radiation strikes at least one of the detectors 124. Each of the one or more of the detectors 124 may have one or more detector elements. In addition, the detectors or detector elements therein may be of different or similar dimension, energy resolution, shape, etc. In one instance, the detectors 124 are large area two-dimensional detectors that can be used to detect data corresponding to multiple slices, larger volumes, widths or regions of interest, etc. relative to one-dimensional detectors. Such detectors 124 can be used to acquire data corresponding to larger areas or whole organs in one axial scan.

At 216, each of the detectors 124 generates a signal indicative of the detected radiation. Since radiation from multiple x-ray sources 108 is concurrently detected, the generated signals have radiation contributions from each of the emitting x-ray sources 108. At 220, these signals are provided to a reconstruction system 136, which reconstructs the signals using various reconstruction techniques to produce volumetric data indicative of the scanned region of the subject. As describe above, the reconstruction system 136 uses the reconstructor 140 to reconstruct the signals. At 224, the volumetric data is processed to generate one or more images that can be displayed, filmed, archived, fused, or otherwise processed.

The systems and methods described herein can be used with CT application in which capturing larger volumes in a relatively short period of time is desired. Such applications include cardiac CT in which it is often desired to image the whole or a substantial portion of the heart relatively quickly to improve temporal resolution. Examples of other applications include perfusion scans, functional scans, metabolic scans, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A computed tomography system, comprising:
   at least two x-ray sources aligned at different z-axis locations at about a same angular position, wherein the at least two x-ray sources concurrently emit radiation that traverses an imaging region;
   at least one detector that detects radiation emitted by the at least two x-ray sources and generates composite data indicative of the detected radiation; and
   a reconstruction system that reconstructs the composite data to generate an image wherein the reconstruction system updates a fractional contribution from the at least two sources for a voxel in the reconstructed data.

2. The system of claim 1, wherein the reconstruction system employs a reconstructor that accounts for contributions from each of the at least two x-ray sources in the composite data.

3. The system of claim 2, wherein the reconstructor employs an iterative reconstruction approach.

4. The system of claim 3, wherein the iterative approach includes maximizing a log-likelihood through at least one of an expectation-maximization, a coordinated decent, an ordered subset, and a paraboloidal technique.

5. The system of claim 1, wherein the at least two x-ray sources emit radiation with about a same photon flux or a different photon flux.

6. The system of claim 1, wherein the at least one detector detects the radiation during a single axial scan.

7. The system of claim 1, wherein the at least two x-ray sources are associated with one of different x-ray tubes, a same x-ray tube, and a combination thereof.

8. The system of claim 1, wherein the detected data corresponds to a portion of a human heart.

9. The system of claim 1, further including at least one additional x-ray source arranged at a different angular position and a different z-axis location.

10. The system of claim 1, further including at least one additional x-ray source arranged at a different angular position and about the same z-axis location of one of the at least two x-ray sources.

11. The system of claim 1, wherein the radiation emitted by the different x-ray sources has different radiation spectral characteristics.

12. The system of claim 1, further including at least a second detector, wherein the at least one detector and the second detector have a similar or different energy resolution.

13. A stereo tube computed tomography imaging method, comprising:
   concurrently emitting radiation by at least two x-ray sources positioned at different z-axis locations at about a same angular position around an imaging region that traverses the imaging region;
   detecting the radiation from the at least two x-ray sources with at least one common detector;
   generating composite data indicative of the detected radiation; and
   reconstructing the composite data using an iterative reconstruction technique that accounts for contributions from each of the at least two x-ray sources in the composite data to form an image.

14. The method of claim 13, wherein the at least two x-ray sources emit radiation with substantially similar photon flux.

15. The method of claim 13, wherein for each voxel in each iteration the step of reconstructing the composite data including:
   computing a contribution from each of the at least two x-ray sources;
   adjusting each contribution based on measured data;
   updating results from a preceding iteration; and
   backprojecting the updated results.

16. The method of claim 15, wherein the back projection is weighted as a function of the x-ray source to the aggregate contribution to account for each of the at least two x-ray sources.

17. The method of claim 13, further including updating the results by maximizing a log-likelihood function.

18. A computed tomography system, comprising:
   at least first and second x-ray sources aligned at different z-axis locations at about a same angular position;
   at least a third x-ray source arranged at a different angular position and at about the same or a different z-axis location, wherein the at least first, second and third x-ray sources concurrently emit radiation that traverses an imaging region;
   at least one detector that detects radiation emitted by the at least first, second and third x-ray sources and generates composite data indicative of the detected radiation; and
   a reconstruction system that reconstructs the composite data to generate an image.

19. A computed tomography system, comprising:
   at least two x-ray sources aligned at different z-axis locations at about a same angular position, wherein the at least two x-ray sources concurrently emit radiation that traverses an imaging region and the radiation emitted by the different x-ray sources has different radiation spectral characteristics;
   at least one detector that detects radiation emitted by the at least two x-ray sources and generates composite data indicative of the detected radiation; and
   a reconstruction system that reconstructs the composite data to generate an image.

20. A computed tomography system, comprising:

at least two x-ray sources aligned at different z-axis locations at about a same angular position, wherein the at least two x-ray sources concurrently emit radiation that traverses an imaging region and the concurrently emitted radiation overlaps such that a voxel is concurrently intersected by radiation from both of the sources;

at least one detector that detects radiation emitted by the at least two x-ray sources and generates composite data indicative of the detected radiation; and a reconstruction system that reconstructs the composite data to generate an image.

* * * * *